United States Patent [19]
Wuelknitz et al.

[11] Patent Number: 5,279,814
[45] Date of Patent: Jan. 18, 1994

[54] ORAL-HYGIENE/DENTIFRICE PREPARATIONS WHICH PROTECT DENTAL ENAMEL

[75] Inventors: Peter Wuelknitz, Langenfeld; Hans Laska, Duesseldorf; Walter Ploeger, Hilden, all of Fed. Rep. of Germany

[73] Assignee: Henkel Kommanditgesellschaft auf Aktien, Duesseldorf, Fed. Rep. of Germany

[21] Appl. No.: 934,671

[22] PCT Filed: Feb. 28, 1991

[86] PCT No.: PCT/EP/0000372

§ 371 Date: Sep. 9, 1992

§ 102(e) Date: Sep. 9, 1992

[87] PCT Pub. No.: WO91/13607

PCT Pub. Date: Sep. 19, 1991

[30] Foreign Application Priority Data

Mar. 9, 1990 [DE] Fed. Rep. of Germany ....... 4007431

[51] Int. Cl.$^5$ .......................... A61K 7/16; A61K 7/18; A61K 7/22
[52] U.S. Cl. ...................... 424/52; 424/49; 424/54
[58] Field of Search ..................... 424/49-58

[56] References Cited

U.S. PATENT DOCUMENTS

| | | | |
|---|---|---|---|
| 3,488,419 | 1/1970 | McCune et al. | 424/49 |
| 3,988,443 | 10/1976 | Ploeger et al. | 424/200 |
| 4,933,173 | 6/1990 | Bristow et al. | 424/49 |
| 5,015,628 | 5/1991 | Reynolds | 424/49 |
| 5,130,123 | 7/1992 | Reynolds et al. | 424/49 |

FOREIGN PATENT DOCUMENTS

| | | |
|---|---|---|
| 0166055 | 1/1986 | European Pat. Off. |
| 2224430 | 12/1973 | Fed. Rep. of Germany |
| 2343196 | 4/1975 | Fed. Rep. of Germany |
| 8203008 | 9/1982 | PCT Int'l Appl. |
| 8707615 | 12/1987 | PCT Int'l Appl. |

OTHER PUBLICATIONS

A Sensitive Pyramidal Diamond Tool, Knoop et al., pp. 39-61, (1939).
D. B. Boyer et al., Remineralozation orf dentin in vitro, Chem. Abstract, (1976).

*Primary Examiner*—Shep K. Rose
*Attorney, Agent, or Firm*—Ernest G. Szoke; Wayne C. Jaeschke; Norvell E. Wisdom, Jr.

[57] ABSTRACT

Combinations of fluoride or monofluorophosphate with phosvitin or soluble salts thereof provide superior protection against demineralization of tooth enamel when used in oral hygiene compositions such as toothpastes and mouthwashes.

3 Claims, No Drawings

ORAL-HYGIENE/DENTIFRICE PREPARATIONS WHICH PROTECT DENTAL ENAMEL

BACKGROUND OF THE INVENTION

1. Field of the Invention

This invention relates to oral and dental hygiene preparations which contain a combination of water-soluble fluorine compounds and phosvitin for protection against demineralization of the enamel.

2. Statement of Related Art

Oral and dental hygiene preparations are products which are used to clean and take care of the mouth, teeth and throat. In addition to the elimination of halitosis and the removal of coatings from the teeth, the function of oral and dental hygiene preparations is to prevent tooth disease, such as caries.

One known strategy is to protect the enamel against, or make it more resistant to, attack. For example, it is known that a thin protein film (the so-called pellicle) on the teeth formed from the constituents of the saliva protects the teeth against excessive mineral losses. It is also known that this protein film consists of phosphoproteins which bear phosphoric acid groups attached to serine and which adhere particularly firmly to the enamel surface. In addition, it is known (WO82/03008) that phosphoproteins can be added to dental care preparations to reduce the dissolution of hydroxyapatite, the main constituent of dental enamel.

It has also long been standard practice to add fluorine in the form of water-soluble fluorides or monofluorophosphates to oral and dental hygiene preparations in order to increase the resistance of the enamel to attack by caries.

DESCRIPTION OF THE INVENTION

Summary of the Invention

It has now surprisingly been found that the enamel-protecting and demineralization-inhibiting effect of fluorine can be considerably improved by even small additions of phosvitin. This is totally unexpected because far weaker effects are obtained with phosphoproteins alone than with fluoride.

Accordingly, the present invention relates to oral and dental hygiene preparations in the form of aqueous, aqueous-alcoholic or water-free compositions which, for protection against demineralization of the enamel, contain a combination of fluoride or monofluorophosphate and phosvitin or water-soluble salts thereof in such a quantity that, when used in the oral cavity, a concentration of at least 0.01% by weight of dissolved fluorine and at least 0.01% by weight of phosvitin is present.

Oral and dental hygiene preparations in the context of the invention are tooth powders, toothpastes, tooth gels, tooth creams, mouthwashes, oral rinses, lozenges and chewing gum.

DESCRIPTION OF PREFERRED EMBODIMENTS

In order to guarantee the minimum concentration of dissolved fluorine and phosvitin according to the invention in the oral cavity, preparations used in undiluted form, for example toothpastes, tooth gels, tooth creams, toothpowders and mouthwashes, must contain 0.01% to 0.2% by weight fluorine in the form of a water-soluble fluoride or monofluorophosphate and 0.01 to 0.4% by weight of phosvitin. This takes into account dilution by the saliva and the water used in the cleaning of teeth.

Mouthwash concentrates should contain a higher concentration of dissolved fluorine and phosvitin corresponding to the intended dilution ratio. Oral and dental hygiene preparations in the form of lozenges or chewing gum, of which the active ingredients are diluted several times with saliva in use, should contain approximately 0.05 to 1% by weight of fluorine in the form of water-soluble fluoride or monofluorophosphate and 0.1 to 2% by weight of phosvitin.

Alkali metal fluorides, for example sodium fluoride, magnesium fluoride, zinc fluoride and tin fluoride, and also fluorides of amino compounds and surface-active quaternary ammonium fluorides may be present as the water-soluble fluorine compounds. Alkali metal monofluorophosphates for example sodium monofluorophosphate, may also be used.

Phosvitin is a glycophosphoprotein which is isolated by known methods from the yolk of birds' and amphibians' eggs and from fish roes. There are various types of phosvitins, a principal phosvitin component having a molecular weight of 34,000 to 36,000 daltons and a smaller component having a molecular weight of about 28,000 daltons being obtainable from hens eggs. All phosvitins are characterized by a high content of phosphated serine (phosphoserine). For a content of about 119 phosphoserine units (more than half the amino acid units) per molecule, phosvitin has a phosphorus content of about 10% by weight and, accordingly, is the most highly phosphated natural protein. Phosvitin is commercially available. Phosvitin may also be used in the form of a water-soluble salt, for example the sodium or ammonium salt.

The oral and dental hygiene preparations according to the invention contain the characteristic combination of dissolved fluorine and phosvitin in a carrier typical of the particular formulation.

In the case of mouthwashes, this carrier consists essentially of water, ethanol, essential oils, emulsifiers and solubilizers, flavor correctants (for example sweeteners) and, optionally, astringent or toning drug extracts, dyes and preservatives. Particularly suitable emulsifiers and solubilizers are ethoxylated sorbitan fatty acid esters, ethoxylated glycerol fatty acid esters, alkyl glucosides, fatty acid polyglycol esters or ethylene oxide/propylene oxide block polymers.

Oral and dental hygiene preparations according to the invention in the form a mouthwash preferably contain 1 to 10% by weight of ethanol in the in-use concentration.

Toothpastes, tooth creams or tooth gels are generally understood to be paste-like preparations of water, consistency regulators, humectants, abrasives or polishes, surfactants, sweeteners, flavorings, deodorizing agents and also agents against mouth and tooth disease. Any of the usual polishes such as, for example, chalk, dicalcium phosphate, insoluble sodium metaphosphate, aluminum silicates, calcium pyrophosphate, fine-pariicle synthetic resins, silicas, aluminum oxide and aluminum oxide trihydrate, may be used in the toothpastes according to the invention. However, oral and dental hygiene preparations according to the invention are preferably in the form of a composition containing abrasives and polishes or a gel containing silicas or aluminum oxide trihydrate as the abrasive and polishing component. These abrasive and polishing components preferably make up 15 to 50% by weight of the toothpastes.

Suitable humectants are, for example, glycerol, sorbitol, xylitol, propylene glycols, polyethylene glycols, particularly those having average molecular weights of 200 to 800. Suitable consistency regulators (or binders) are, for example, natural and/or synthetic water-soluble polymers, such as carragheenates, tragacanth, starch and starch ethers, cellulose ethers such as, for example, carboxymethyl cellulose (Na salt), hydroxyethyl cellulose, methyl hydroxypropyl cellulose, guar, acacia gum, agar agar, xanthan gum, carob bean flour, pectins, water-soluble carboxyvinyl polymers (for example Carbopol ® types), polyvinyl alcohol, polyvinyl pyrrolidone and polyethylene glycols, particularly those having molecular weights of 1,500 to 1,000,000.

Other suitable viscosity regulators are, for example, layer silicates such as, for example, montmorillonite clays, colloidal thickening silica such as, for example, aerogel silica or pyrogenic silicas.

Suitable surfactants are any water-soluble, anionic, cationic, ampholytic, zwitterionic and nonionic surfactants. Preferred surfactants are the nonionic surfactants already mentioned, more particularly the ethoxylated sorbitan fatty acid esters, the ethoxylated glycerol fatty acid esters, for example castor oil ethoxylates, alkyl glucosides, fatty acid polyglycol esters and ethylene oxide/propylene oxide copolymers.

Other typical toothpaste additives are
  preservatives and antimicrobial agents such as, for example, p-hydroxybenzoic acid methyl, ethyl or propyl ester, sodium sorbate, sodium benzoate, bromochlorophene, phenyl salicylic acid ester, thymol, etc.
  anti-scale agents, for example organophosphates, such as the sodium salts of 1-hydroxyethane-1,1-diphosphonic acid, azacycloheptane-1,1-diphosphonic acid, 1-phosphonopropane-1,2,3-tricarboxylic acid and other carboxylic acids, for example those known from U.S. Pat. No. 3,488,419, DE-OS 2 224 430 and DE-OS 2 343 196,
  sweeteners such as, for example, saccharin sodium, sodium cyclamate, sucrose, lactose, maltose, fructose,
  flavorings such as, for example, peppermint oil, spearmint oil, eucalyptus oil, anise oil, fennel oil, caraway oil, menthyl acetate, cinnamic aldehyde, anethol, vanillin, thymol and mixtures of these and other natural and synthetic flavorings,
  pigments, such as titanium dioxide for example,
  dyes,
  buffers such as, for example, primary, secondary or tertiary alkali metal phosphates or citric acid/sodium citrate,
  wound-healing and inflammation-inhibiting substances such as, for example, allantion, urea and also azulene, camomile-based agents, acetyl salicylic acid derivatives.

The following Examples are intended to illustrate the invention.

EXAMPLES

Testing of the Demineralization of Dental Enamel

1. Test method

The principle of the test is based on the observation that the strength of the enamel is reduced by demineralization. This loss of strength can be determined by the method of indentation hardness measurement. The measuring principle is based on measurement of the depth of penetration of a diamond of defined geometry which is pressed vertically into the test material under a certain weight. The so-called KNOOP method was used, leaving behind a diamondshaped indentation in the material (Knoop, F., Peters, C. G., Emerson, W. B., "A Sensitive Pyramidal Diamond Tool for Indentation Measurements", $J. Res. Natn. Bur. Stand.$ 23, 39–61 (1939)). The greater the depth penetration, the more advanced the demineralization process. In the in vitro method used, the natural demineralization and remineralization processes are simulated on bovine enamel.

2. Method 2.1 Preparation of the enamel blocks

The fronts of bovine incisors are cut into pieces measuring 3×5 mm (slabs) and are mounted with wax on Plexiglas ™ cubes (1×2.5×2.5 cm) in such a way that only the enamel surface remains exposed. The enamel surface is polished until it appears uniformly smooth. Four slabs are used per test group.

2.2 Treatments

The in vitro test used begins with a 7-hour demineralization phase (lactic acid solution) followed by a 16 hour remineralization phase (remineralizing solution). These treatment steps are repeated three times. The phosvitin is present in both solutions in the concentration indicated. If fluoride is used in a test group, it is applied by immersion of the slabs for 5 minutes in NaF solution having the concentration shown in Table I before each individual treatment phase.

Demineralizing Solution 100 ml of 1M lactic acid and 500 mg of hydroxyapatite were adjusted with NaOH solution to a pH value of 4.6 and, after addition of phosvitin in the quantity shown in Table 1, were made up with distilled water to 1 liter.

Remineralizing Solution (Synthetic Saliva)

| |
|---|
| 654 mg $KH_2PO_4$, |
| 825.5 mg $Na_2HPO_4.2H_2O$, |
| 1168 mg NaCl |
| 2354 mg KCl and |
| 540 mg $CaCl_2.2H_2O$ | were dissolved in distilled water, adjusted to pH 5 with 1M NaOH or HCl solution and, after addition of phosvitin in the quantity shown in Table I, were made up to 2 liters with distilled water.

2.3 Indentation hardness measurements

The measurement was carried out with a KNOOP diamond under a weight of 55 kg on untreated tooth and after each treatment phase. The result is expressed as the length of the large indentation diagonal in μm.

2.4 Calculation of the data

The differences between the indentation length after the individual treatments and before beginning of the treatments were determined for each individual slab. The respective average values of the four-slab test groups were then related to the average value of the control group (no protein or fluoride) in accordance with the following formula:

$$EDR = \frac{\text{Difference indentation length test group}}{\text{Difference indentation length control group}} \times 100$$

Accordingly, the EDR value (enamel demineralization reduction) expresses the percentage reduction in demineralization by comparison with the control.

3. Results

The enamel demineralization reduction values for the individual test groups are shown in the order of the demineralization and remineralization steps.

Table 1 shows how strong protective effects by comparison with the control occur in the repeated demineralization and remineralization steps through treatment with 250 ppm dissolved fluorine (0.055 % by weight of NaF).

Where only 0.02 % by weight of phosvitin is used, these effects are comparatively weak; where 0.1% by weight of phosvitin is used, they are much stronger, but for the most part weaker than with fluoride alone.

The combination of the treatment with phosvitin and fluoride produces a strong additional protective effect which clearly surpasses the favorable effect of fluoride, even with the low phosvitin concentration. The combined use of phosvitin and fluoride makes the tooth substantially immune to demineralization. Since phosvitin is superior to the pellicle proteins by virtue of its greater number of binding groups, there are advantages in using the combination according to the invention with anti-caries fluorides in all dental and oral hygiene preparations.

TABLE 1

| Group | 1 | 2 | 3 | 4 | 5 |
|---|---|---|---|---|---|
| NaF (% by weight) | 0.055 | — | — | 0.055 | 0.055 |
| Phosvitin (% by weight) | — | 0.02 | 0.1 | 0.02 | 0.1 |
|  | EDR | EDR | EDR | EDR | EDR |
| 7 Hours demin. | 16 | 29 | 54 | 58 | 84 |
| 16 Hours remin. | 18 | 27 | 33 | 69 | 74 |
| 7 Hours demin. | 47 | 22 | 61 | 72 | 89 |
| 16 Hours remin. | 40 | 17 | 48 | 78 | 85 |
| 7 Hours demin. | 65 | 33 | 60 | 84 | 91 |
| 16 Hours remin. | 71 | 35 | 55 | 86 | 88 |
| 7 Hours demin. | 76 | 19 | 62 | 88 | 91 |
| 16 Hours remin. | 81 | 28 | 59 | 92 | 92 |

4. Application Examples 4.1 Mouthwash I

| | |
|---|---|
| Ethanol (99%, non-denatured) | 7.5% by weight |
| Phosvitin (SIGMA) | 0.4% by weight |
| Sodium fluoride | 0.22% by weight |
| HR 60[1] | 0.25% by weight |
| Flavoring oil (peppermint) | 0.2% by weight |
| Aspartame | 0.1% by weight |
| Dye, blue C.I.42090 (1% in $H_2O$) | 0.1% by weight |
| PHB methyl ester | 0.1% by weight |
| PHB propyl ester | 0.02% by weight |
| Water ad | 100.00% by weight |

4.2 Mouthwash II

| | |
|---|---|
| Ethanol (99%, non-denatured) | 5.0% by weight |
| Phosvitin (SIGMA) | 0.1% by weight |
| Sodium monofluorophosphate | 1.2% by weight |
| HR 60[1] | 0.5% by weight |
| Flavoring oil (peppermint) | 0.3% by weight |
| Aspartame | 0.1% by weight |
| Dye, red C.I.16255 (1% in $H_2O$) | 0.1% by weight |
| PHB methyl ester | 0.1% by weight |
| PHB propyl ester | 0.02% by weight |
| Water ad | 100.00% by weight |

4.3 Tooth cream

| | |
|---|---|
| Aluminum oxide trihydrate | 50.0% by weight |
| Glycerol 86% | 10.0% by weight |
| Na carboxymethyl cellulose | 1.2% by weight |
| Titanium dioxide | 1.0% by weight |
| Phosvitin (SIGMA) | 1.0% by weight |
| Sodium fluoride | 0.11% by weight |
| HR 60[1] | 0.5% by weight |
| Flavoring oil (citrus) | 0.3% by weight |
| Saccharin sodium | 0.05% by weight |
| PHB methyl ester | 0.15% by weight |
| PHB propyl ester | 0.05% by weight |
| Water ad | 100.00% by weight |

[1] Adduct of 60 moles of ethylene oxide with hydrogenated castor oil

The invention claimed is:

1. Oral and dental hygiene compositions, comprising a combination of fluoride or monofluorophosphate and phosvitin or soluble salts thereof in such a quantity that, when used in the oral cavity, a concentration of 0.01 to 0.2% by weight of dissolved fluorine and 0.01 to 0.4% by weight of phosvitin is present.

2. Oral and dental hygiene compositions as claimed in claim 1 in the form of a toothpaste or a gel, comprising silicas or aluminum oxide trihydrate as an abrasive and polishing component.

3. An oral and dental hygiene composition as claimed in claim 1 in the form of a mouthwash, wherein, in its in-use concentration, the mouthwash contains 1 to 10% by weight of ethanol.

* * * * *